United States Patent [19]

Cremonese

[11] Patent Number: 4,839,292
[45] Date of Patent: Jun. 13, 1989

[54] CELL CULTURE FLASK UTILIZING A MEMBRANE BARRIER

[76] Inventor: Joseph G. Cremonese, 227 Maple Dr., Greensburg, Pa. 15601

[21] Appl. No.: 95,759

[22] Filed: Sep. 11, 1987

[51] Int. Cl.$^4$ .............................................. C12M 1/04
[52] U.S. Cl. .................................. 435/313; 435/311; 435/290
[58] Field of Search ................ 435/313, 240, 284, 68, 435/29, 285; 215/DIG. 3; 206/0.6

[56] References Cited

U.S. PATENT DOCUMENTS

| | | | |
|---|---|---|---|
| 3,407,120 | 10/1968 | Weiss et al. | 195/104 |
| 3,449,210 | 6/1969 | Rohde | 195/139 |
| 3,537,956 | 11/1970 | Falcone et al. | 195/139 |
| 3,821,087 | 6/1974 | Knazek et al. | 195/127 |
| 3,870,602 | 3/1975 | Froman et al. | 195/139 |
| 3,941,662 | 3/1976 | Munder et al. | 195/127 |
| 4,142,940 | 3/1979 | Modolell et al. | 195/139 |
| 4,201,845 | 5/1980 | Feder et al. | 435/285 |
| 4,208,483 | 6/1980 | Lee | 435/284 |
| 4,225,671 | 9/1980 | Puchinger et al. | 435/71 |
| 4,228,243 | 10/1980 | Iizuka | 435/285 |
| 4,296,205 | 10/1981 | Verma | 435/240 |
| 4,334,028 | 6/1982 | Carver | 435/284 |
| 4,440,853 | 4/1984 | Michaels et al. | 435/68 |
| 4,559,299 | 12/1985 | Rotman | 435/29 |
| 4,634,676 | 1/1987 | Sapatino | 435/294 |

*Primary Examiner*—Larry Jones
*Attorney, Agent, or Firm*—Webb, Burden, Ziesenheim & Webb

[57] ABSTRACT

A cell culture flask includes a hollow housing and a gas permeable membrane disposed within the housing which divides the housing into a first chamber and a second chamber. A retaining ring secures the gas permeable membrane within the housing and forms a liquid-tight seal between the first chamber and the second chamber. A gas inlet in the housing communicates with the first chamber and supplies gas thereto. A media inlet in the housing communicates with the second chamber and provides cell growth media thereto.

28 Claims, 6 Drawing Sheets

CELL CULTURE FLASK UTILIZING A MEMBRANE BARRIER

DESCRIPTION

1. Field of the Invention

This invention relates to a culture flask for the culturing of cells and, more particularly, to a two chamber flask with a gas permeable membrane separating the two chambers.

2. Description of the Prior Art

The culturing of living cells in vitro is commonly carried out for a variety of purposes, such as medical, biological or genetic research. Typically, the cells are grown in media which contains nutrients and other constituents required for cell metabolism, growth and proliferation. Subsequently the cells and/or their by-products may be removed from the media and utilized or analyzed.

A variety of devices for culturing cells are known in the art. U.S. Pat. Nos. 4,225,671 and 3,941,662 disclose devices in which a gas permeable membrane forms one complete surface of a culture container. However, the membrane vessel structures are complex to assemble and costly to manufacture. U.S. Pat. No. 4,201,845 discloses a cell culture reactor which is formed of an open-topped housing having media inlet ports, a gas inlet port and a gas outlet port. A lid has a media outlet port and an access port for sampling or inoculation. A layer of gas permeable hollow fibers is positioned in the lower housing and is supported on a plate having a plurality of holes. The gas inlet port and gas outlet port each communicate directly with the hollow fibers for aeration of the inside of the fibers and the media flows around the hollow fibers. However, such hollow fibers in laboratory scale culturing are rather cumbersome to use and the device of such is expensive to manufacture. In addition, grown cells are difficult to remove intact from a layer of hollow fibers which are characteristically somewhat fragile.

Accordingly, it is an object of the present invention to provide a cell culture flask which has an inexpensive growth surface which is easy to manufacture and from which the cells can be removed simply and intact.

Typically, a biologist or medical researcher will stain the cells for study under a microscope. This involves a tedious process of transferring the cells to a microscope slide and then fixing and staining the cells. Cells may become distorted, damaged or ajuxtaposed in transferring them from a flask or other standard vessel to a microscope slide, thus making cell study and/or observation inconvenient and possibly incomplete.

It is yet another object of the present invention to provide a cell culture flask having a growth surface which permits the cultured cells to be transferred intact and directly stained rather than transferring the cells to a microscope slide. Additionally, the membrane itself can be used in place of a microscope viewing slide.

It is a further object of this invention to provide a cell culture flask that can cooperate with an incubator in a manner to efficiently grow cell culture with a minimal amount of human contact.

SUMMARY OF THE INVENTION

Accordingly, I have invented a cell culture flask which includes a hollow housing and a gas permeable membrane disposed within the housing and dividing the housing into a first chamber and a second chamber. A retaining means for removably securing the gas permeable membrane within the housing is provided and forms a liquid-tight seal between the first chamber and the second chamber. A gas inlet is provided into the housing and communicates with the first chamber for supplying gas thereto. A media inlet is provided into the housing and communicates with the second chamber for providing cell growth media thereto. The cell culture flask can include a media outlet from the housing that communicates with the second housing for discharging cell growth media therefrom.

In one embodiment the cell culture flask has a housing which is an open-topped structure having a base and a peripheral wall. The retaining means is a retaining ring conforming to an inner geometric diameter of the peripheral wall. The membrane is frictionally held in place by compressing an outer perimeter of the membrane between an outer surface of the retaining ring and an inner surface of the housing. A gas outlet from the housing that communicates with the first chamber can also be included.

In another embodiment the housing is an open-topped structure having a base, a peripheral outer wall and a peripheral inner wall. The retaining means is a retaining ring conforming to a perimeter of the peripheral inner wall. The membrane is frictionally held in place by compressing an outer perimeter of the membrane between a surface of the retaining ring and a surface of the peripheral inner wall. The first chamber is below the membrane and within the peripheral inner wall. Preferably, a portion of the retaining ring rests against a portion of the peripheral outer wall and forms an intermediate chamber. The retaining ring forms a liquid and gas seal between the intermediate chamber and the second chamber. The gas inlet communicates with the intermediate chamber and the peripheral inner wall has an opening positioned below the retaining ring and in fluid communication with the intermediate chamber.

Another embodiment is an open-bottomed structure having a top and a peripheral wall. The membrane is positioned over the bottom. The retaining means is a retaining ring conforming to the perimeter of the peripheral wall. The membrane is frictionally held in place by compressing an outer perimeter of the membrane between a surface of the retaining ring and a surface of the peripheral wall. The retaining ring can also have a bottom surface that is adapted to rest on a base unit that has means for supplying gas to the first chamber.

Another embodiment is an open-topped hollow housing that includes a base and a peripheral wall. A gas permeable membrane is disposed over the open top and the peripheral wall of the housing. A retaining ring is provided for securing the gas permeable membrane about an outer surface of the peripheral wall. The retaining ring conforms to an outer geometric diameter of the peripheral wall. The membrane is frictionally held in place by compressing an outer perimeter of the membrane between an inner surface of the retaining ring and an outer surface of the housing. Also, the retaining ring extends above the peripheral wall. A first chamber is formed below the membrane and a second chamber is formed above the membrane and within the inner surface of the retaining ring. A gas inlet is provided into the housing and communicates with the first chamber for supplying gas thereto.

The gas permeable membrane utilized in accordance with this invention can be transparent so that cultured cells may be stained on the membrane and viewed and studied under a microscope. In addition, the flasks may also be transparent in order that the cells may be observed during the culturing process.

BRIEF DESCRIPTION OF THE DRAWINGS

Like reference numerals are used throughout with like parts.

DESCRIPTION OF THE PREFERRED EMBODIMENTS

Figure 1:
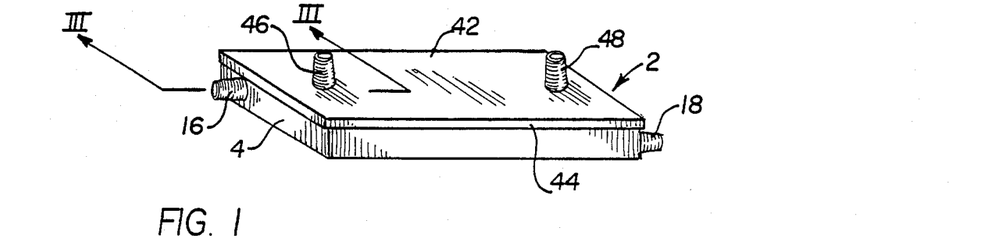
FIG. 1 is a perspective view of a first embodiment of a cell culture flask in accordance with the present invention.
Figure 2:
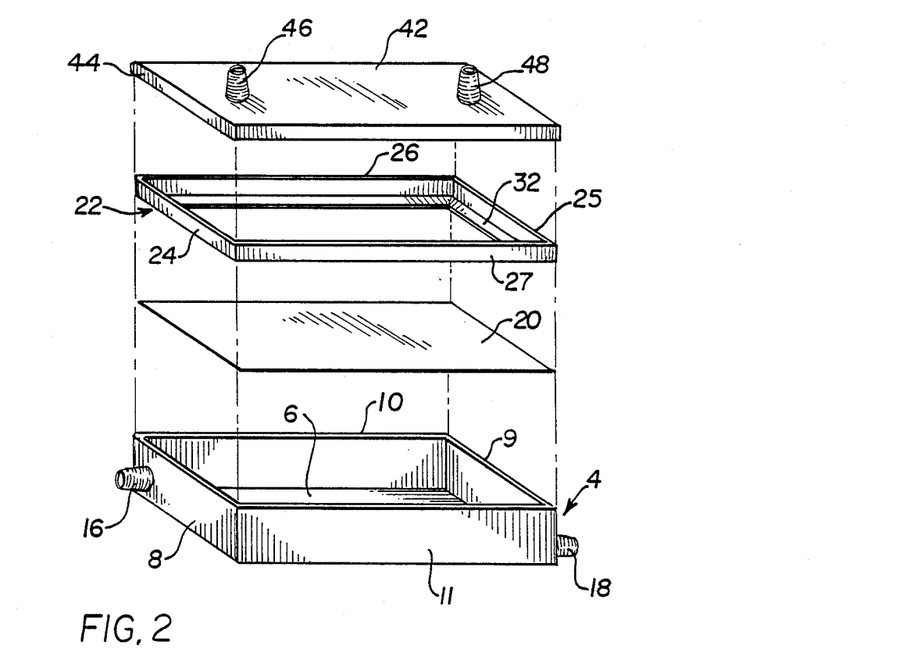
FIG. 2 is an exploded perspective view of the cell culture flask shown in FIG. 1.
Figure 3:
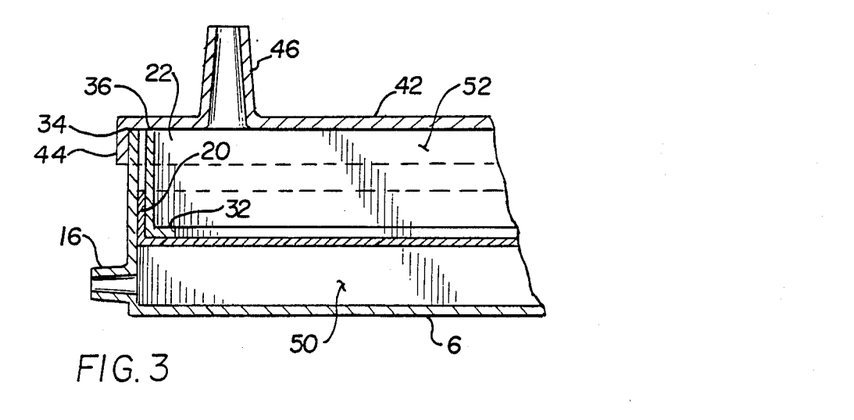
FIG. 3 is a section taken along lines III—III in FIG. 1.

Referring to FIGS. 1-3, there is shown a first embodiment of a cell culture flask 2 in accordance with the present invention. The cell culture flask 2 includes an open-topped, hollow housing 4. The housing 4 is preferably rectangularly-shaped and includes a base 6 and a peripheral wall formed of opposed and parallel walls 8 and 9, and walls 10 and 11 opposed and parallel to each other. Wall 10 and wall 11 are connected between walls 8 and 9. The walls 8-11, all about the same height, extend upwardly from the base 6 along its outer peripheral edges and are integral therewith.

Wall 8 includes a gas inlet 16 therethrough, preferably located near a lower corner adjacent wall 10. Wall 9 includes a gas outlet 18 therethrough, preferably located near a lower corner adjacent wall 11. The gas inlet 16 and gas outlet 18 are preferably diagonally opposed to each other in order to optimize gas flow through the cell culture flask 2. The gas inlet 16 and gas outlet 18 may be hollow nipples as shown in the figures, or may be any similar device for establishing fluid flow through the housing 4.

A gas permeable membrane 20 is positioned within the housing 4. The gas permeable membrane 20 is rectangularly-shaped and somewhat larger than the outer dimensions of base 6. The gas permeable membrane 20 is made from any material which is impervious to liquids, promotes cell growth thereon and permits the flow of gas therethrough. Suitable materials include fluorinated ethylene propylene copolymers, polycarbonates, polyethylene copolymers, ethylene copolymers, polypropylene and fluroplastics. The membrane may be treated to promote the adherence of cells to the membrane, such as etching a surface of the membrane.

The gas permeable membrane 20 is positioned above the base 6 of the housing 4 and also above the gas inlet 16 and the gas outlet 18 and is held in place by a retaining ring 22. The retaining ring 22 is rectangularly-shaped and includes opposed and parallel side walls 24 and 25 and walls 26 and 27 which are opposed and parallel to each other. Side walls 26 and 27 are positioned between and connected to side walls 24 and 25. Side walls 24 and 25 are also perpendicular to side walls 26 and 27. An inwardly oriented lower lip 32 formed at the lower edge of side walls 24-27 may be an integral portion of the retaining ring 22. The height of the height of the walls 8-11 of the housing 4. The outer dimensions of the retaining ring 22 are slightly smaller than the inner dimensions of the housing 4 so that the retaining ring 22 may be positioned within the housing 4.

The lower lip 32 of the retaining ring 22 is in contact with the gas permeable membrane 20 and walls 24-27 of the retaining ring 22 compress the outer perimeter of the membrane 20 against walls 8-11 of the housing 4 so that the retaining ring 22 and the membrane 20 are held in place within the housing 4 by frictional engagement. A top edge 34 of the housing 4 is preferably aligned with a top edge 36 of the retaining ring 22.

A lid 42 having a rectangular shape slightly larger than the peripheral wall formed by walls 8-11 is positioned on top of the housing 4 inclusive of the retaining ring 22. The lid 42 has a downwardly directed lip 44 which extends around an outer perimeter of the lid 42. The lip 44 of the lid 42 is adjacent the outer surface of walls 8-11 and functions to align the lid 42 onto the housing 4. The lid 42 also includes a media inlet 46 and a media outlet 48 extending therethrough and can be molded into the lid 42. The media inlet 46 and media outlet 48 alternatively may extend through one of the side surfaces. The media inlet 46 and the media outlet 48 are spaced apart on the lid 42 so that an optimum flow of cell culture media may be supplied to an upper surface of the gas permeable membrane 20. The media inlet 46 and media outlet 48 may be hollow nipples as shown, although other liquid flow connectors may be used including inwardly oriented ports.

In this arrangement, the cell culture flask 2 is divided into two chambers, a bottom or first chamber 50 between the gas permeable membrane 20 and the base 6 of the housing 4, and a top or second chamber 52 between the gas permeable membrane 20 and the lid 42. A liquid-tight seal is formed between the bottom chamber 50 and the top chamber 52 by the gas permeable membrane 20 and the retaining ring 22.

The cell culture flask 2 shown in FIGS. 1-3 is used to grow cells as follows: The gas permeable membrane 20 is positioned within the housing 4 and is held in place by the retaining ring 22. A sample of cell culture is placed in the top chamber 52 onto a top surface of the gas permeable membrane 20. The lid 42 is then positioned on the housing 4. Cell culture media is supplied to the top chamber 52 through media inlet 46 and will exit through the media outlet 48. A supply gas line is connected to the gas inlet 16 and an exit gas line is connected to the gas outlet 18. The gas supplied may be any gas suitable for cell growth such as oxygen, carbon dioxide or nitrogen, or a mixture of these gases. The gas is supplied to the gas inlet 16 at a pressure equal to or higher than the gas exiting through the gas outlet 18. This permits the gas to pass through the bottom chamber 50. The exit line from the gas outlet 18 may be restricted or closed completely to allow pressurized gas to remain in the lower chamber while the flow is interrupted for predetermined intervals. The gas pressure in the bottom chamber 50 is also higher than the gas pressure in the top chamber 52 and enables a portion of the gas supplied to the bottom chamber 50 to permeate through the gas permeable membrane 20. Thus, the growing cells are directly supplied with gas. Gas also bubbles through the media, resulting in an aeration of the media in the top chamber 52.

The gas will also exit the flask 2 through both the media outlet 48 and the interface between the lip 44 of the lid 42 and walls 8-11 of the housing 4. Gas waste products produced by the cells during growth are released from the flask 2 in a similar fashion.

Although the flask 2 of this embodiment discloses an aerobic cell culture arrangement, anaerobic cell cultures can also be accommodated by eliminating the gas supply to the gas inlet 16 and sealing gas inlet 16 and gas outlet 18.

The liquid growth media is supplied to the top chamber 52 through the media inlet 46. The media rests above the cells which are on the top surface of the gas permeable membrane 20. A constant supply of fresh media may be supplied to the flask 2 through the media inlet 46 and spent media may be removed from the flask 2 through the media outlet 48.

When the cells have incubated for a desired period of time, the media is removed and the gas permeable membrane 20, now having a layer of cells thereon, is removed intact either by cutting the membrane 20 about its outer edges or by removing the retaining ring 22 from the housing 4 and removing the entire gas permeable membrane 20.

Preferably, the gas permeable membrane 20 is transparent so that the cells may be directly fixed, stained and viewed under a microscope. The transparent membrane with cells may be mounted on various sizes of glass or plastic matrices, i.e., a 75 mm.×25 mm. microscope slide, for convenient handling or viewing. This arrangement provides a quick and efficient means for cell study since there is little risk of disrupting the cells such as is possible in conventional cell culturing where the cells are mechanically or enzymatically removed and transferred from the flask/media to microscope slides.

Figure 4:
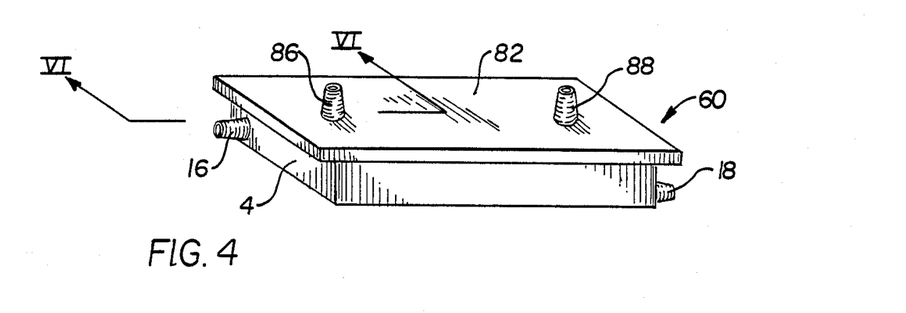
FIG. 4 is a perspective view of a second embodiment of a cell culture flask in accordance with the present invention.
Figure 5:
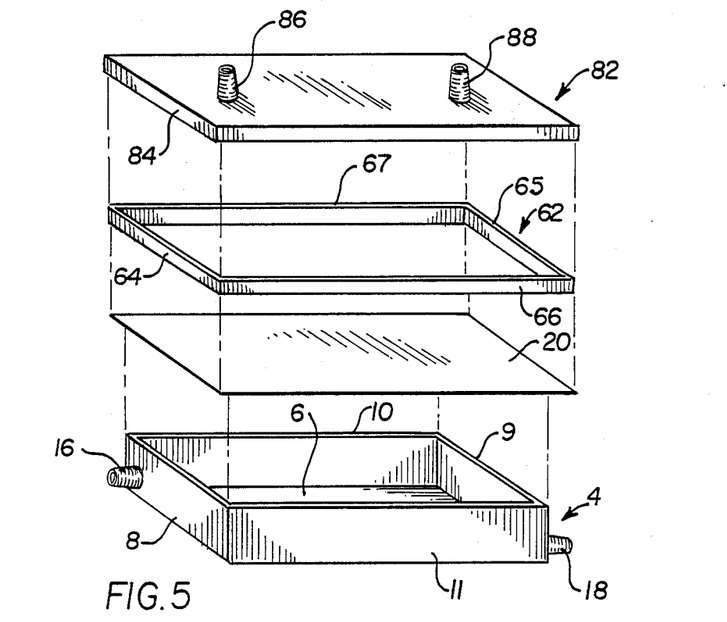
FIG. 5 is an exploded perspective view of the cell culture flask shown in FIG. 4.
Figure 6:
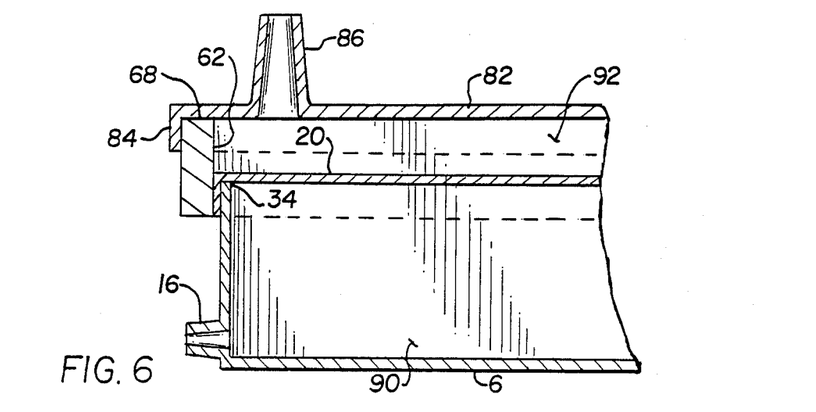
FIG. 6 is a section taken along lines VI—VI in FIG. 4.

A second embodiment of the cell culture flask 60 in accordance with the present invention is shown in FIGS. 4-6. This embodiment utilizes the same housing 4 and the same gas permeable membrane 20 as that of the flask 2. Accordingly, like reference numerals are used for like parts in this embodiment. The gas permeable membrane 20 is positioned above the base 6 of the housing 4. The membrane 20 is also positioned above the gas inlet 16 and the gas outlet 18 and rests on the top edge 34 of the housing 4 so that it extends over walls 8-11 of the housing 4. The membrane 20 is held in place by a retaining ring 62. The retaining ring 62 is rectangularly-shaped and includes opposed and parallel walls 64 and 65 and walls 66 and 67 which are opposed and parallel to each other. Walls 66 and 67 are positioned between and connected to walls 64 and 65. Walls 64 and 65 are also perpendicular to walls 66 and 67. The inner dimensions of the retaining ring 62 are slightly larger than the outer dimensions of the housing 4 so that the retaining ring 62 may be positioned around the outer perimeter of the housing 4 about walls 8-11.

Walls 64-67 of the retaining ring 62 compress the outer perimeter of the membrane 20 against the outer surfaces of walls 8-11 of the housing 4 so that the retaining ring 62 and the membrane 20 are held in place. The top edge 34 of the housing 4 is positioned below a top edge 68 of the retaining ring 62.

A lid 82 having a rectangular shape slightly larger than the outer geometric diameter of the retaining ring 62 formed by walls 64-67 is positioned on top edge 66 of the retaining ring 62. The lid 82 has a downwardly directed lip 84 which extends around an outer perimeter of the lid 82. The lip 84 of the lid 82 is adjacent the outer surfaces of walls 64-67 of the retaining ring 62 and functions to align the lid over the housing 4. The lid 82 also includes a media inlet 86 and a media outlet 88 extending therethrough and can be molded into the lid 82. The media inlet 86 and the media outlet 88 are spaced apart on the lid 82 so that an optimum flow of cell culture media may be supplied to an upper surface of the membrane 20. The media inlet 86 and the media outlet 88 may be hollow nipples as shown, although other liquid flow connectors may be used, including inward oriented ports.

In this arrangement, the cell culture flask 60 is divided into two chambers, a bottom or first chamber 90 between the gas permeable membrane 20 and the base 6 of the housing 4, and a top or second chamber 92 between the gas permeable membrane 20 and the lid 82. A liquid-tight seal is formed between the bottom chamber 90 and the top chamber 92 by the gas permeable membrane 20 and retaining ring 62.

An outwardly extending stop although not necessary may be provided on an outer surface of walls 8-11 of the housing 4 so that a bottom edge of the retaining ring rests thereon. This insures that the top edge 68 of the retaining ring 62 extends above the top edge 34 of the housing 4. Alternatively, an inwardly extending stop although not necessary may be provided on an inner surface of walls 64-67 of the retaining ring 62 so that the retaining ring 62 can rest on a portion of the upper surface of the membrane 20 which is directly above and supported by walls 8-11 of the housing 4. This also insures that the top edge 68 of the retaining ring 62 extends above the top edge 34 of the housing 4.

The cell culture flask 60 shown in FIGS. 4-6 is used to grow cells as follows: The gas permeable membrane 20 is positioned over the top edge 34 of the housing 4 and is held in place by the retaining ring 62 by frictional engagement. A sample of cell culture is placed in the top chamber 92 onto a top surface of the gas permeable membrane 20. The lid 82 is then positioned on the housing 4. Cell culture media is supplied to the top chamber 92 through media inlet 86 and will exit through the media outlet 88. A supply gas line is connected to the gas inlet 16 and an exit gas line is connected to the gas outlet 18. The gas supplied may be any gas suitable for cell growth such as oxygen, carbon dioxide or nitrogen, or a mixture of these gases. The gas is supplied to the gas inlet 16 at a pressure equal to or higher than the gas exiting through the gas outlet 18. This permits the gas to pass through the bottom chamber 90. The gas pressure in the bottom chamber 90 is also higher than the gas pressure in the top chamber 92 and enables a portion of the gas supplied to the bottom chamber 90 to permeate through the gas permeable membrane 20. Thus, the growing cells are directly supplied with gas. Gas also bubbles through the media, resulting in an aeration of the media in the top chamber 92.

The gas will also exit the flask 60 through both the media outlet 88 and the interface between the lip 84 of the lid 82 and walls 64-67 of the retaining ring 62. Gas waste products produced by the cells during growth are released from the flask 60 in a similar fashion.

Although the flask 60 of this embodiment discloses an aerobic cell culture arrangement, anaerobic cell cultures can also be accommodated by eliminating the gas supply to the gas inlet 16 and sealing gas inlet 16 and gas outlet 18.

The liquid growth media is supplied to the top chamber 92 through the media inlet 86. The media rests above the cells which are on the top surface of the gas permeable membrane 20. A constant supply of fresh media is supplied to the flask 60 through the media inlet 86, while spent media is removed from the flask 60 through the media outlet 88.

When the cells have incubated for a desired period of time, the media is removed and the gas permeable membrane 20, now having a layer of cells thereon, is removed intact either by cutting the membrane 20 about its outer edges or by removing the retaining ring 62 from the housing 4 and removing the entire gas permeable membrane 20.

Figure 7:
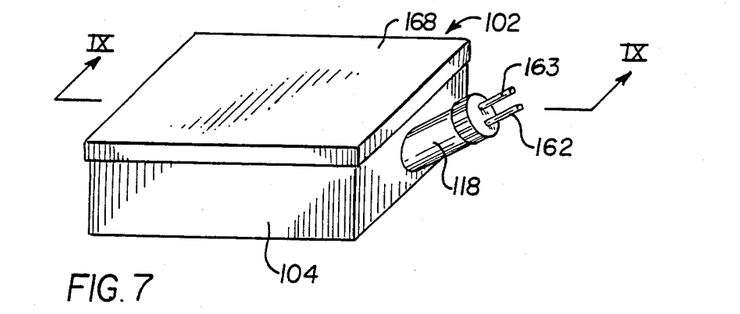
FIG. 7 is a perspective view of a third embodiment of a cell culture flask in accordance with the present invention.
Figure 8:
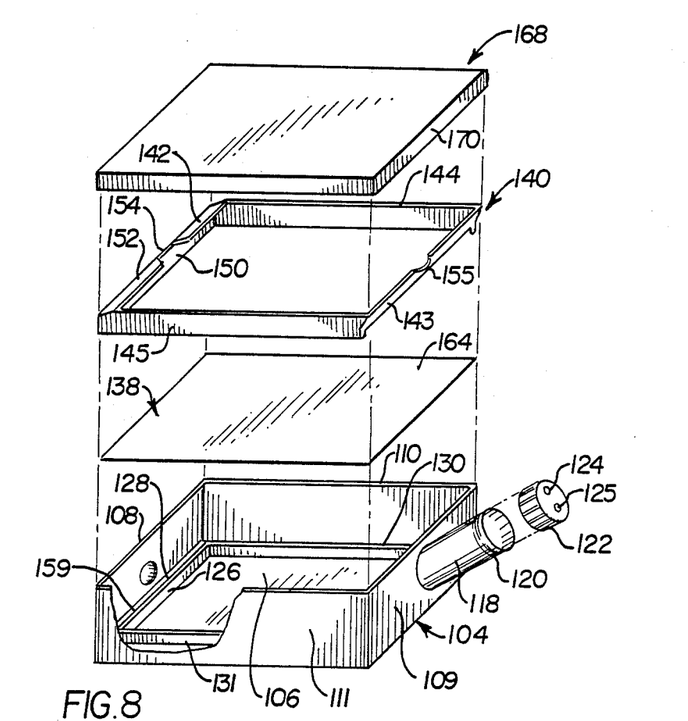
FIG. 8 is an exploded perspective view of the cell culture flask shown in FIG. 7.
Figure 9:
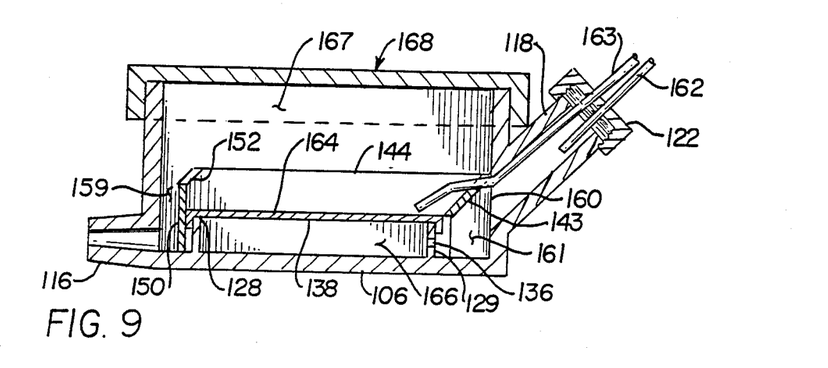
FIG. 9 is a section taken along lines IX—IX in FIG. 7.

A third embodiment of a cell culture flask 102 in accordance with the present invention is shown in FIGS. 7-9. The cell culture flask 102 includes an open-topped, hollow housing 104. The housing 104 is preferably rectangularly-shaped and includes a base 106, and a peripheral wall formed of opposed and parallel walls 108 and 109 and walls 110 and 111 opposed and parallel to each other. Wall 110 and wall 111 are connected between walls 108 and 109. Walls 108-111, all about the same height, extend upwardly from the base 106 along its outer peripheral edges and are integral therewith. An outlet port 116 may be provided at a lower end of wall 108, possibly as a "knock-out" blank, and an inlet port 118 is provided on wall 109.

The inlet port 118 is a hollow, cylindrically-shaped member having a threaded outer end 120. The inlet port 118 is angled upwardly and away from wall 109. An end cap 122 is threaded onto the outer end 120 of the inlet port 118. The end cap 122 has a media inlet bore 124 and a gas inlet bore 125 extending therethrough.

The flask 102 also includes a rectangular inner peripheral wall 126 which extends upwardly from and is integrally formed to the base 106 of the housing 104. The inner peripheral wall 126 has four inner walls 128-131 which are adjacent to but spaced slightly from walls 108-111, respectively. Inner wall 129 has an opening 136 which is positioned substantially in front of the inlet port 118.

The flask 102 includes a gas permeable membrane 138 which extends across and contacts the inner peripheral wall 126 and is held in place by a retaining ring 140. The gas permeable membrane 138 has the same physical and chemical properties as the gas permeable membrane 20 of the flask 2 discussed above in connection with FIGS. 1-3. The gas permeable membrane 138 is rectangularly-shaped and is geometrically similar to but slightly larger than the inner peripheral wall 126.

The retaining ring 140 is rectangularly-shaped and has side walls 142-145 which, when in place, are adjacent to inner walls 128-131, respectively. Side walls 142, 144 and 145 of the retaining ring 140 are substantially equal in height and are taller than the inner peripheral wall 126. Side walls 142, 144 and 145 also rest on the base 106 of the housing 104. Side wall 144 and side wall 145 of the retaining ring 140 are substantially vertical and parallel to each other. Side wall 142 of the retaining ring 140 is formed from a first section 150 positioned below and integral with a second section 152. The first section 150 is substantially vertical and extends between side walls 144 and 145 of the retaining ring 140 and rests on the base 106 of the housing 104. The second section 152 is positioned above the inner peripheral wall 126 and slopes inwardly toward the interior of the retaining ring 140. A drainage notch 154 is located in the center of the second section 152. The drainage notch 154 has an open top and inwardly sloping sides. The side wall 143 of the retaining ring 140 slopes outwardly from a position slightly below the top of wall 129 of the inner peripheral wall 126 to the top of the retaining ring 140. An arcuate-shaped inlet notch 155 is provided on an upper edge of side wall 143.

The retaining ring 140 sandwiches the gas permeable membrane 138 between an upper outer surface of inner peripheral walls 128-131 and a lower inner surface of the first section 150 of the side wall 142 and lower surfaces of side walls 143-145 of the retaining ring 140. Although the membrane is positioned on the upper outer surface of peripheral walls 128-131, the membrane is positioned away from the opening 136 of inner wall 129 so that gas can flow therethrough. The outer surfaces of side walls 145 and 144 of the retaining ring 140 are adjacent to and in contact with the inner surfaces of the walls 111 and 110 of the base member 104, respectively, forming a substantial ga and liquid seal therebetween. Inner wall 128 of the inner peripheral wall 126 is positioned away from wall 108 and forms an outlet space 159 therebetween. Inner wall 129 of the inner peripheral wall 126 is positioned away from the second side wall 109 and forms an inlet space therebetween. A top surface of side wall 143 of the retaining ring 140 is adjacent to and in contact with an inner surface of wall 110 of the housing 104. An intermediate chamber 161 is defined as being below the side wall 143 and between walls 110 and 111. The inlet port 118 is in fluid communication with the intermediate chamber 161. The opening 136 in inner wall 129 is also in fluid communication with the intermediate chamber 161. The inlet notch 155 is positioned below and directly in front of an upper portion of the inlet port opening 160. Also, the drainage notch 154 is positioned directly in front of media outlet 116.

A gas inlet line 162 enters through the gas inlet bore 125 of the threaded end cap 122 and extends into inlet port 118. A media inlet line 163 extends in turn through the media inlet bore 124, the inlet port 118 and the inlet notch 155. In this manner, cell culture media can be supplied to an upper surface of the gas permeable membrane 138. A substantially gas-tight seal is formed at an interface of the inlet port 118, side wall 143 of the retaining ring 140 and the media inlet line 163. A bottom or first chamber 166 is formed below the gas permeable membrane 138 and an upper or second chamber 167 is formed above the membrane 138.

Finally, a lid 168 having a downwardly directed outer lip 170 is positioned on an upper surface of the housing 104. The lip 170 aligns the lid 168 with the walls 108-111 of the housing 104.

In operation, the gas permeable membrane 138 is held in place on the rectangular inner peripheral wall 126 by the retaining ring 140. A sample of cell culture is placed onto the upper surface 164 of the gas permeable membrane 138. The threaded end cap 122 is fastened to the end 120 of the inlet port 118. Inlet media line 163 is passed through both the media inlet port 125 and the inlet notch 155 on the retaining ring 140. The gas inlet line 162 is passed into the gas inlet port 118. Appropriate suction means, or provisions for gravity draining, are attached to the outlet port 116. Finally, the lid 168 is positioned on the housing 104.

Gas is supplied from the gas inlet line 162 through the inlet port 118, through the intermediate chamber 161, through opening 136 and then into the bottom chamber 166. Much of the gas then permeates through the gas permeable membrane 138. Media is supplied to the upper surface 164 of the gas permeable membrane 138 through media inlet line 163. A constant height of media is maintained on the gas permeable membrane 138 by the retaining ring 140 as determined by the depth of the drainage notch 154. The drainage notch 154 enables the media overflow to accumulate in the outlet space 159. The media is subsequently removed through the outlet port 116. In this manner fresh media may be continually supplied to the cell culture flask 102. Excess gas is either removed through the outlet port 116 or escapes from the interface between the lip 170 of the lid 168 and the walls 108-111 of the base member 104. Although the flask 102 of this embodiment discloses an aerobic cell culture arrangement, anaerobic cell cultures can also be accommodated by eliminating the gas inlet bore 125 from the threaded end cap 120.

Figures 10, 11:
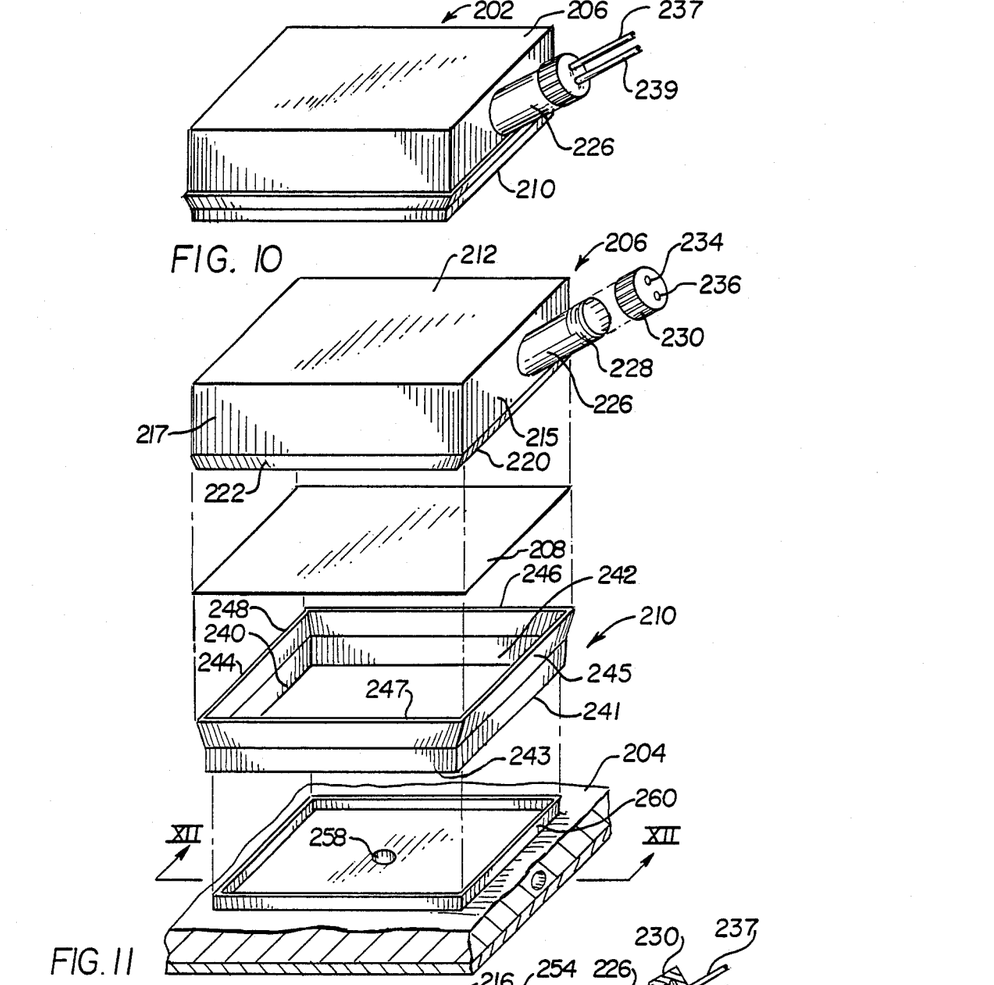
FIG. 10 is a perspective view of a fourth embodiment of a cell culture flask in accordance with the present invention.
FIG. 11 is an exploded perspective view of the cell culture flask shown in FIG. 10 positioned on a base unit.
Figure 12:
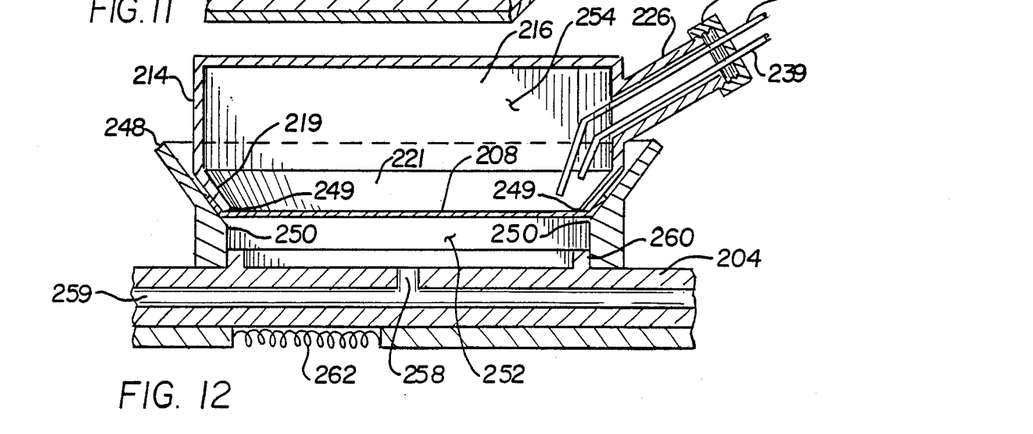
FIG. 12 is a section taken along lines XII—XII in FIG. 11.

A fourth embodiment of a cell culture flask 202 is shown in FIGS. 10-12 positioned on a gas supplying and supporting base 204. The flask 202 includes a hollow, open-bottomed housing 206, a gas permeable membrane 208 and a retaining ring 210. The housing 206 is preferably rectangularly-shaped and includes a flat top 212 and a peripheral wall extending downwardly therefrom and including opposed and parallel walls 214 and 215 and walls 216 and 217 opposed and parallel to each other. Inwardly sloping sections 219, 220, 221 and 222 are attached to the bottom edges of walls 214-217, respectively, of the housing 206.

An upwardly sloping, hollow, cylindrical neck 226 is integrally attached to wall 215 of the housing 206. The neck 226 has an externally threaded end 228 and receives an end cap 230 having internal threads. The end cap 230 has a media inlet bore 234 and a media outlet bore 236 therethrough. A media inlet tube 237 extends through the media inlet bore 234 and a media outlet tube 239 extends through the media outlet bore 236. The media inlet tube 237 and the media outlet tube 239 are securely held in place by bores 234 and 236 so that an effective gas seal is formed by the end cap 230.

The retaining ring 210 is a rectangularly-shaped structure and includes a side wall 240 substantially parallel with and opposed to side wall 241. Likewise, side wall 242 is opposed and substantially parallel to side wall 243. Outwardly sloping sections 244, 245, 246, and 247 are integrally attached to the top edges of side walls 240-243, respectively, of the retaining ring 210. Outwardly sloping sections 244-247 of the retaining ring 210 form a shape which is geometrically similar to the shape formed by inwardly sloping sections 219-222 of the housing 206. However, a top surface 248 of outwardly sloping sections 244-247 has a larger geometric diameter than a bottom surface 249 of the inwardly sloping sections 219-222 of the housing 206 and a lower surface 250 of outwardly sloping sections 244-247 has a smaller geometric diameter than the bottom surface 249 of the housing 206 so that the sloping sections 244-247 of the retaining ring 210 can be received by the sloping sections 219-222 of the housing 206.

The gas permeable membrane 208 is rectangularly-shaped and is positioned in the retaining ring 210 above walls 240-243. The membrane 208 is compressed and frictionally held in place between the inwardly sloping sections 219-222 of the housing 206 and the outwardly sloping sections 244-247 of the retaining ring 210. A bottom or first chamber 252 is formed below the membrane 208 and a top or second chamber 254 is formed above the membrane 208.

The flask 202 is adapted to be placed on a flat base 204 or other supporting surface. The base 204 may include a gas orifice 258 or other gas supplying means and the retaining ring 210 is positioned over the gas orifice 258. FIGS. 11-12 show one embodiment for the base 204. Gas is supplied to the gas orifice 258 through a gas manifold 259 located in the base 204. An aligning ring 260 is located on the top surface of the base 204 to position the flask 202 over the gas orifice 258 and keep the flask 202 from moving about. The aligning ring 260 is rectangularly-shaped and has vertical walls. An outer surface of the aligning ring 260 cooperates with inner surfaces of side walls 240-243 of the retaining ring 210. The base 204 may also include a heating coil 262 or the like for heating the gas passing through the manifold 259.

In operation, a cell culture is supplied to an upper surface of the gas permeable membrane 208 which is then compressed and frictionally held in place, about its outer perimeter, between the inwardly sloping sections 219-222 of the housing 206 and the outwardly sloping sections 244-247 of the retaining ring 210. Gas is supplied to the bottom chamber 252 of the flask 202 by the gas manifold 259 and orifice 258. Culture media is supplied to the top chamber 254 by media inlet tube 237. Spent media is removed by the media outlet tube 239 which uses suction to transport cell culture media from the cell culture flask 202. Gas permeates through the membrane 208 and through the media. In this embodiment the gas is expelled between the threads of the end cap 230 and threads of the cylindrical neck 226. This is accomplished by loosening the end cap 230 on the threaded end 228 of the cylindrical neck 226. For optimum cell growth the incoming gas and base 204 are maintained at a proper temperature by the heating coil 262. Although the flask 202 of this embodiment discloses an aerobic cell culture arrangement, anaerobic cell cultures can also be accommodated by eliminating the gas manifold 259 and orifice 258 of the base 204.

Figure 13:
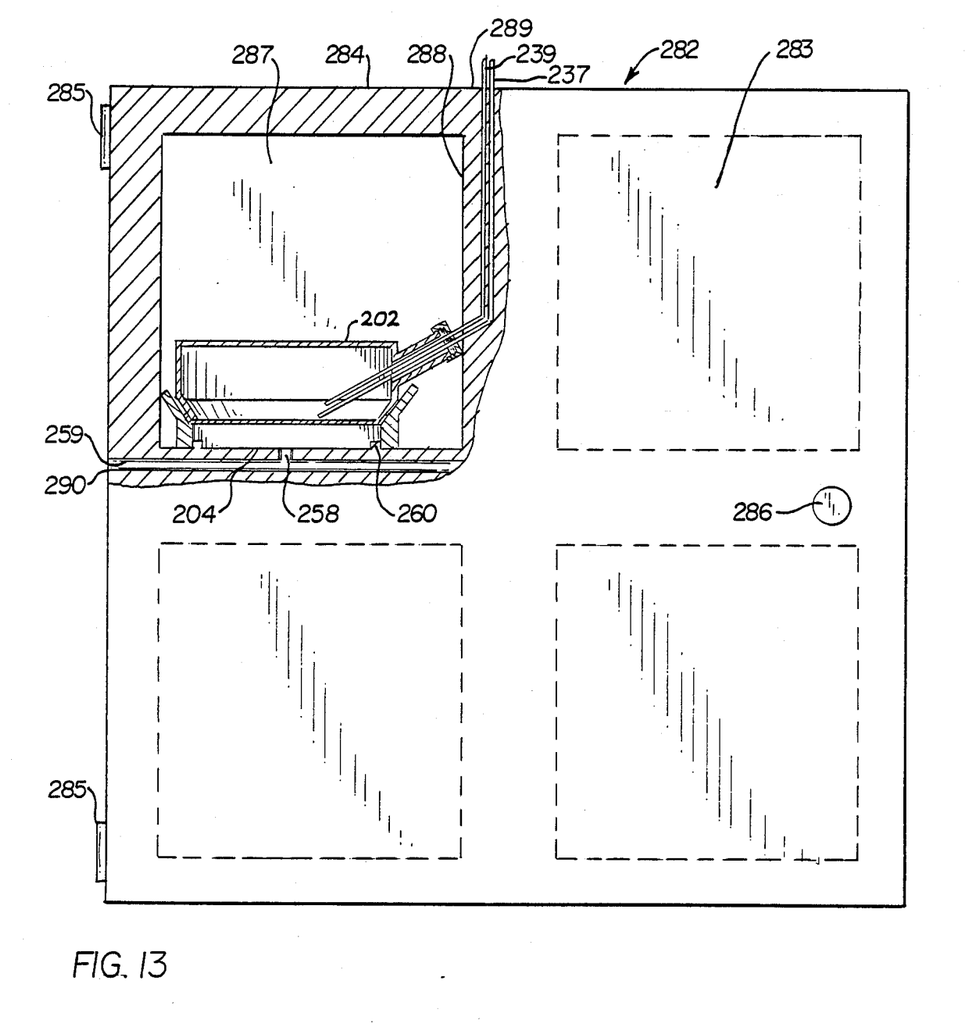
FIG. 13 is a front view, partially in section, of a cell culture apparatus in accordance with the present invention.

All of the flasks 2, 60, 102 and 202 shown in FIGS. 1-12 may be used in a multi-chamber, sealed incubator. Cell culture media and gas can be supplied to the flasks in the incubators. In this manner, the environment for cell culture growth can be controlled to optimize conditions for cell growth, such as a uniform temperature inside and outside of the flasks. In addition, human contact with the flasks is minimized. This reduces the chance of contamination between the cell culture and the outside environment. An example of one such incubator is shown in FIG. 13. Incubator 282 has four compartments adapted to receive flask 202, although any number of compartments can be used and incubators can be designed to accommodate flask 2 and flask 102.

The incubator 282 is a box-like structure having a front door 283. Each compartment is insulated with insulation material 284 and is provided with the flat base 204. The door 283 is attached to the body of the incubator by hinges 285. A handle 286 is attached to the door for ease of opening and closing the door 283. Upper compartment 287 shows the cell culture flask 202 positioned on the aligning ring 260 of the base 204. The media inlet tube 237 and media outlet tube 239 for the upper compartment 287 run along an inner wall 288 of the incubator 282 and exit from a top 289 of the incubator 282. Gas is supplied to the upper compartment 287 through the gas manifold 259. The gas enters at an entrance port 290 found on one side of the incubator 282. Gas which escapes from the flasks 202 leaks from the incubator 282 along the perimeter of door 283 and into the atmosphere. When the cell culture has matured the media inlet tube 237 and media outlet tube 239 are removed from the flask 202. The flask is then removed from the incubator 282 so that the incubated cells can be stained and studied.

As described above, any flask according to this invention can be received by an incubator having any number of chambers. The incubator may require other hardware than is shown in FIG. 13 to supply to the flasks the proper cell growth gases and cell growth media and analyze the spent cell culture media and gas to monitor the cell growth in the flasks.

Figure 14:
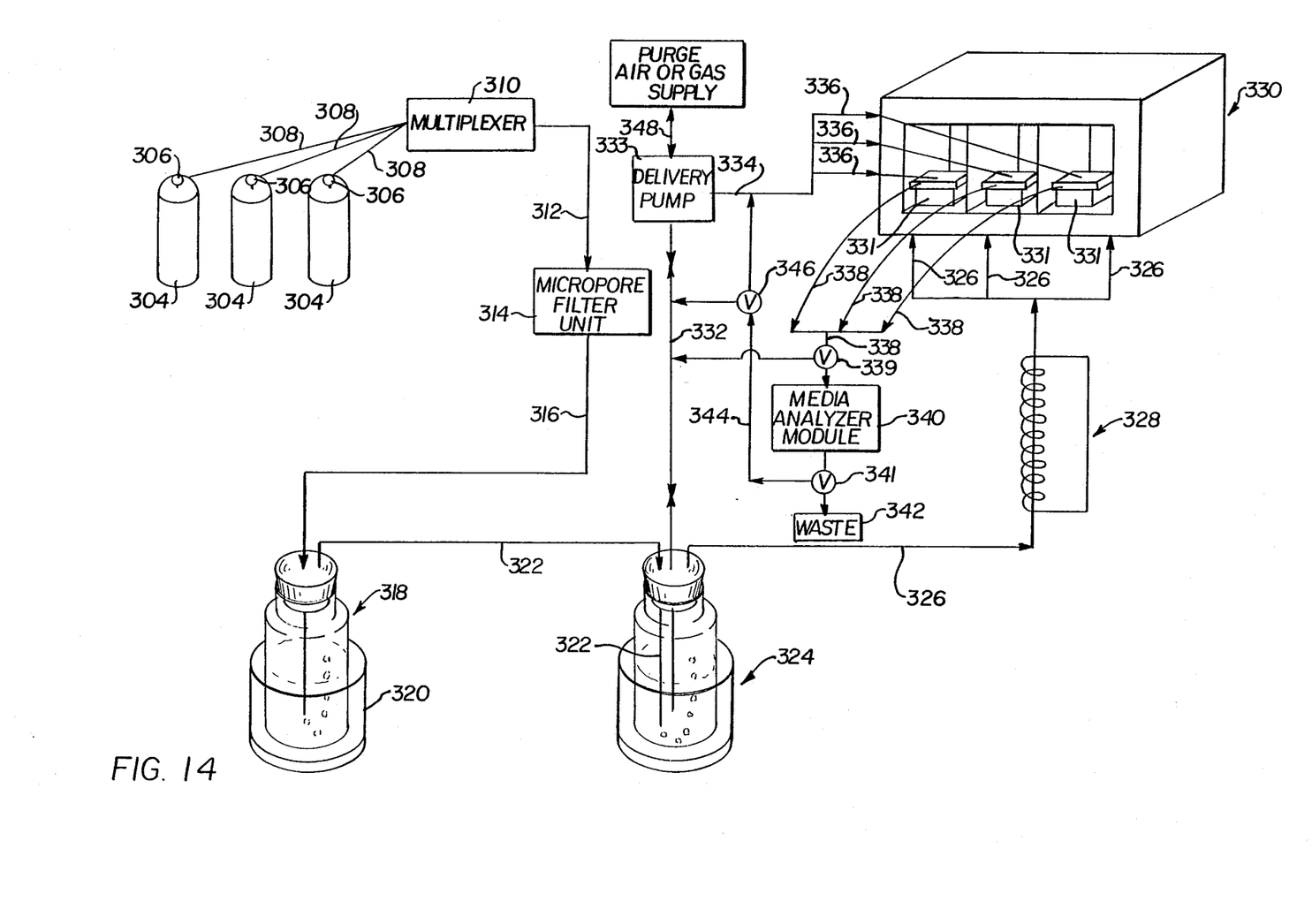
FIG. 14 is a schematic diagram of a cell culturing system in accordance with the present invention.

FIG. 14 illustrates a cell culture system utilizing a cell culture flask having a gas permeable membrane, an incubator and means for supplying the flasks with the proper gases and media for optimum cell growth. This system includes a plurality of gas cylinders 304 which contain oxygen, nitrogen, carbon dioxide, or any other gas required for cell growth. The gas flow from the cylinders 304 is regulated by gas flow regulators 306. A supply line 308 from each cylinder 304 transports the gas to a multiplexer 310 where the gases are blended together as desired for a particular application. The gas is then transported by gas line 312 to a micropore filter unit 314 to filter the blended gas. The gas is then transported through gas line 316 to a gas humidifier 318. The humidifier 318 may also be preheated by a heater 320 to heat the incoming gas. The humidified gas passes through gas line 322 to a heated media receptacle 324. The gas is bubbled through the receptacle 324 and exits through gas line 326. The gas may be heated again by heater 328 in order to heat the gas to an optimum temperature for cell growth. Finally, the gas is supplied to an incubator 330 and distributed to each of the cell culture flasks 331.

Heated media exits the media receptacle 324 through media transport line 332. The media is drawn from the receptacle by a delivery pump 333, such as a peristaltic pump. The media then passes through transport line 334 to a media manifold 336 and then to the flasks 331 in the incubator 330. Spent media may also be removed from the cell culture flasks 331 through media outlet lines 338 and pass through a multi-directional valve 339 which either directs the spent media to transport line 332 for reuse or delivers the spent media to a module 340 which analyzes the chemical composition and pH of the media. From module 340, the media is then directed by a valve 341 to either a waste disposal 342 or transported through a media transport line 344 for reuse. A multi-directional valve 346 can direct the spent media from transport line 344 to media transport line 332 and deposit the media into the media receptacle 322 for further use. The multi-directional valve 346 can also direct the media from transport line 344 to media transport line 334 and supply the media directly to the media manifold 336. Finally, the delivery pump 333 may be reversed to change the flow direction and purge the cell culture flasks 331 of gas or air. The purged gases are transported through the media manifold 336 and media transport line 334 and then through a purge line 348 for removal from the system.

Any suitable material may be used to manufacture the flasks according to this invention, other than the gas permeable membrane. Preferably, the flasks should be made of a transparent material, such as glass or plastic, so that an operator can observe the culture growth without taking apart the flasks.

Having described the presently preferred embodiments of the present invention, it is to be understood that it may be otherwise embodied within the scope of the appended claims.

I claim:

1. A cell culture flask comprising a hollow housing, a gas permeable and liquid impervious membrane disposed within said housing and dividing said housing into a first chamber and a second chamber, retaining means for removably securing said gas permeable membrane within said housing and forming a liquid-tight seal between said first chamber and said second chamber, a gas inlet into said housing and communicating with said first chamber for supplying gas thereto, and a media inlet into said housing and communicating with said second chamber for supplying cell growth media thereto.

2. The cell culture flask of claim 1 further including a media outlet from said housing and communicating with said second chamber for discharging cell growth media therefrom.

3. The cell culture flask of claim 2 wherein said hollow housing is an open-topped structure having a base and a peripheral wall and said retaining means is a retaining ring conforming to an inner geometric diameter of said peripheral wall, said membrane being frictionally held in place by compressing an outer perimeter of said membrane between an outer surface of said retaining ring and an inner surface of said housing.

4. The cell culture flask of claim 3 further including a lid removably positioned on said housing and spaced above said membrane.

5. The cell culture flask of claim 4 wherein said media inlet and media outlet extend through said lid and communicate with said second chamber.

6. The cell culture flask of claim 2 wherein said membrane is transparent.

7. The cell culture flask of claim 2 further including a gas outlet from said housing and communicating with said first chamber.

8. The cell culture flask of claim 2 wherein said housing is an open-topped structure having a base, a peripheral outer wall and a peripheral inner wall; said retaining means is a retaining ring conforming to a perimeter of said peripheral inner wall, said membrane being frictionally held in place by compressing an outer perimeter of said membrane between a surface of said retaining ring and a surface of said inner wall; and said first chamber being below said membrane and within said peripheral inner wall.

9. The cell culture flask of claim 8 wherein a portion of said retaining ring rests against a portion of said peripheral outer wall forming an intermediate chamber, said retaining ring forms a liquid and gas seal between said intermediate chamber and said second chamber, said gas inlet communicates with said intermediate chamber and said peripheral inner wall has an opening positioned below said retaining ring and in fluid communication with said intermediate chamber.

10. The cell culture flask of claim 9 further including an inlet port into said peripheral outer wall communicating with said intermediate chamber.

11. The cell culture flask of claim 10 wherein said inlet port is adapted to receive a media inlet line and said retaining ring has a notch adapted to receive said media inlet line, said notch being of sufficient diameter to form a seal with said media inlet line between said second chamber and said intermediate chamber.

12. The cell culture flask of claim 10 wherein said port has a removable cap on its outer end, said cap being adapted to receive a media inlet line and a media outlet line.

13. The cell culture flask of claim 8 wherein said retaining ring has a drainage notch positioned at a predetermined height, and a media outlet into said housing and communicating with said drainage notch whereby said media is maintained at a particular height in said second chamber on said membrane by said drainage notch and excess media flows from said drainage notch into said media outlet.

14. The cell culture flask of claim 8 further including a lid removably positioned on said housing and spaced above said retaining ring.

15. The cell culture flask of claim 2 wherein said hollow housing is an open-bottomed structure having a top and a peripheral wall, said membrane positioned over said bottom, and
said retaining means is a retaining ring conforming to the perimeter of said peripheral wall, said membrane being frictionally held in place by compressing an outer perimeter of said membrane between a surface of said retaining ring and a surface of said peripheral wall.

16. The cell culture flask of claim 15 wherein said retaining ring has a bottom surface that is adapted to rest on a base unit that has means for supplying gas to said first chamber.

17. The cell culture flask of claim 16 wherein the base unit has an aligning ring adapted to receive said retaining ring and position said flask on the base unit.

18. The cell culture flask of claim 15 wherein a bottom portion of said peripheral wall slopes inwardly and an upper portion of said retaining ring slopes outwardly and receives said bottom portion of said peripheral wall, said membrane being frictionally held in place by compressing an outer perimeter of said membrane between said inward sloping portion of said peripheral wall and said outward sloping portion of said retaining ring.

19. The cell culture flask of claim 15 further comprising:
a neck extending through said housing and communicating with said second chamber, an end cap received by said neck and adapted to receive a media outlet tube and a media inlet tube, whereby said media inlet tube and said media outlet tube may be urged through said end cap into said second chamber and positioned at different heights above said membrane to control the height of media resting on said membrane, and said end cap may be tightened to prevent gas from escaping from said second chamber and loosened to permit gas to escape from said second chamber.

20. A cell culture flask comprising:
an open-topped, hollow housing having a base and a peripheral wall;
a gas permeable and liquid impervious membrane disposed within said housing above said base and dividing said housing into a first chamber and a second chamber;
a removable retaining ring conforming to an inner geometric diameter of said peripheral wall, said membrane being frictionally held in place between an outer surface of said retaining ring and an inner surface of said housing whereby a liquid-tight seal is formed between said first chamber and said second chamber;
a gas inlet and a gas outlet into said housing and communicating with said first chamber; and
a lid removably positioned on said housing and spaced above said membrane, with said lid having a media inlet and a media outlet therethrough and communicating with said second chamber.

21. A cell culture flask comprising:
an open-topped hollow housing that includes a base and a peripheral wall;
a gas permeable and liquid impervious membrane disposed over the open top and said peripheral wall of said housing;
a retaining ring for removably securing the gas permeable membrane about an outer surface of said peripheral wall, said retaining ring conforming to an outer geometric diameter of said peripheral wall, said membrane being frictionally held in place by compressing an outer perimeter of said membrane between an inner surface of said retaining ring and an outer surface of said housing, and said retaining ring extending above said peripheral wall;
a first chamber formed below said membrane;
a second chamber formed above said membrane and within the inner surface of the retaining ring; and
a gas inlet into said housing and communicating with said first chamber for supplying gas thereto.

22. The cell culture flask of claim 21 further comprising a gas outlet from said housing and communicating with said first chamber.

23. The cell culture flask of claim 21 further including a lid removably positioned on said retaining ring and spaced above said membrane.

24. The cell culture flask of claim 23 further including a media inlet and a media outlet that extend through said lid and communicate with said second chamber.

25. An apparatus for cell culture growth comprising:
a cell culture flask including a hollow housing, a gas permeable and liquid impervious membrane disposed within said housing and dividing said housing into a first chamber and a second chamber, a retaining means for removably securing said gas permeable membrane within said housing and forming a liquid-tight seal between said first chamber and said second chamber; a gas inlet into said housing and communicating with said first chamber for supplying gas thereto; and a media inlet into said housing and communicating with said second chamber for supplying cell growth media thereto;

an incubator for receiving one or more of said culture flasks, said incubator having means to permit gas exiting from said flask to exit said incubator, said incubator having means for supplying media to each of said flasks and said incubator having means for supplying gas to each of said flasks;

at least one gas source under pressure;

means for blending the gas and selectively controlling the gas flow to said flasks; and a pump for depositing liquid media into said flasks.

26. The apparatus for cell culture growth of claim 25 further including:

a gas filter positioned immediately downstream of said blending means;

a gas humidifier positioned immediately downstream of said filter; and a gas heater positioned immediately downstream of said gas humidifier.

27. The apparatus for cell culture growth of claim 25, further comprising:

a removal pump to remove the media from said flasks; a media analyzer positioned downstream of said removal pump; and an alternative position control valve positioned downstream of said media analyzer whereby one position of said valve purges the media from said apparatus and a second position permits reuse of the media.

28. The apparatus for cell culture growth of claim 25 wherein said cell culture flask hollow housing is an open-bottomed structure having a top and a peripheral outer wall, said membrane positioned over said bottom, said retaining means is a retaining ring conforming to the perimeter of said peripheral wall, said membrane is frictionally held in place by compressing an outer perimeter of said membrane between a surface of said retaining ring and a surface of said outer wall, and said retaining ring also has a bottom surface that rests upon a base of said incubator and gas is supplied through said base to said first chamber.

* * * * *

UNITED STATES PATENT AND TRADEMARK OFFICE
CERTIFICATE OF CORRECTION

PATENT NO. : 4,839,292

DATED : June 13, 1989

INVENTOR(S) : Joseph G. Cremonese

It is certified that error appears in the above-identified patent and that said Letters Patent is hereby corrected as shown below:

Column 4 Line 24 after "The height of" insert --side walls 24-27 of the retaining ring 22 is less than--.

Column 8 Line 40 "ga" should read --gas--.

Signed and Sealed this

Tenth Day of April, 1990

Attest:

HARRY F. MANBECK, JR.

*Attesting Officer*      *Commissioner of Patents and Trademarks*

REEXAMINATION CERTIFICATE (2385th)

United States Patent [19]
Cremonese

[11] B1 4,839,292
[45] Certificate Issued Sep. 13, 1994

[54] CELL CULTURE FLASK UTILIZING MEMBRANE BARRIER

[76] Inventor: Joseph G. Cremonese, 227 Maple Dr., Greensburg, Pa. 15601

Reexamination Request:
No. 90/003,134, Jul. 15, 1993

Reexamination Certificate for:
Patent No.: 4,839,292
Issued: Jun. 13, 1989
Appl. No.: 95,759
Filed: Sep. 11, 1987

Certificate of Correction issued Apr. 10, 1990.

[51] Int. Cl.$^5$ ............................................. C12M 1/04
[52] U.S. Cl. ................................... 435/313; 435/290; 435/311
[58] Field of Search ............... 435/313, 311, 290, 240, 435/284, 68, 29, 285; 215/DIG. 3; 206/0.6

[56] References Cited

U.S. PATENT DOCUMENTS

| | | | |
|---|---|---|---|
| 4,033,825 | 7/1977 | Haddad et al. | 435/284 |
| 4,225,671 | 9/1980 | Puchinger et al. | |
| 4,537,860 | 8/1985 | Tolbert et al. | 435/240 |
| 5,010,014 | 4/1991 | Gebhardt | |
| 5,028,541 | 7/1991 | Kiel et al. | 435/286 |

*Primary Examiner*—Larry Jones

[57] ABSTRACT

A cell culture flask includes a hollow housing and a gas permeable membrane disposed within the housing which divides the housing into a first chamber and a second chamber. A retaining ring secures the gas permeable membrane within the housing and forms a liquid-tight seal between the first chamber and the second chamber. A gas inlet in the housing communicates with the first chamber and supplies gas thereto. A media inlet in the housing communicates with the second chamber and provides cell growth media thereto.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–28 is confirmed.

* * * * *